United States Patent
Joshi et al.

(10) Patent No.: US 10,925,864 B2
(45) Date of Patent: Feb. 23, 2021

(54) STABLE LIQUID INJECTABLE SOLUTION OF MIDAZOLAM AND PENTAZOCINE

(71) Applicant: NEON LABORATORIES LIMITED, Mumbai (IN)

(72) Inventors: Neeta Joshi, Mumbai (IN); Shailesh Sevankar, Mumbai (IN)

(*) Notice: Subject to any disclaimer, the term of this patent is extended or adjusted under 35 U.S.C. 154(b) by 53 days.

(21) Appl. No.: 16/085,454

(22) PCT Filed: Apr. 1, 2016

(86) PCT No.: PCT/IN2016/050102
§ 371 (c)(1),
(2) Date: Sep. 14, 2018

(87) PCT Pub. No.: WO2017/013677
PCT Pub. Date: Jan. 26, 2017

(65) Prior Publication Data
US 2019/0076411 A1    Mar. 14, 2019

(30) Foreign Application Priority Data

Jul. 18, 2015  (IN) .................. 2723/MUM/2015

(51) Int. Cl.
| | | |
|---|---|---|
| *A61K 31/439* | (2006.01) | |
| *A61K 31/5517* | (2006.01) | |
| *A61K 9/00* | (2006.01) | |
| *A61K 47/02* | (2006.01) | |
| *A61K 47/12* | (2006.01) | |
| *A61K 47/18* | (2017.01) | |
| *A61K 9/08* | (2006.01) | |

(52) U.S. Cl.
CPC .......... *A61K 31/439* (2013.01); *A61K 9/0019* (2013.01); *A61K 9/08* (2013.01); *A61K 31/5517* (2013.01); *A61K 47/02* (2013.01); *A61K 47/12* (2013.01); *A61K 47/183* (2013.01)

(58) Field of Classification Search
CPC .. A61K 31/439; A61K 31/5517; A61K 47/02; A61K 47/12; A61K 47/183; A61K 9/0019; A61K 9/08
See application file for complete search history.

(56) References Cited

U.S. PATENT DOCUMENTS

| | | | |
|---|---|---|---|
| 2003/0073665 A1* | 4/2003 | Thompson | A61K 9/0019 514/58 |
| 2007/0104791 A1* | 5/2007 | Popov | A61K 9/0043 424/488 |
| 2011/0046116 A1 | 2/2011 | Cukrowski | |
| 2013/0309306 A1* | 11/2013 | Rogawski | A61K 31/55 424/489 |

FOREIGN PATENT DOCUMENTS

EP    2 450 039 A1    5/2011

OTHER PUBLICATIONS

Rao et al. 2000, Indian Journal of Urology, vol. 17, Issue 1, pp. 41-43. (Year: 2000).*
Hospira Pentazocine Lactate Injection, USP (Talwin® Injection) Oct. 2008 (Year: 2008).*
Bahadur, N., et al. "Sedation with Combination of Midazolam, Pentazocine and Propofol for Colonoscopy in Outdoor Patients", Medical Journal of Shree Birendra Hospital, vol. 11, pp. 7-9. (Jul.-Dec. 2012).
Short, T.G., et al. "Propofol and Midazolam Act Synergistically in Combination", British Journal of Anaesthesia, 67, pp. 539-545. (1991).
International Search Report and Written Opinion of the International Searching Authority dated Aug. 5, 2016 in connection with PCT/IN2016/050102, filed Apr. 1, 2016.
Good, et al., "The Compatibility and Stability of Midazolam and Dexamethasone in Infusion Solutions", Journal of Pain and Symptom Management, vol. 27, No. 5, pp. 471-475. (May 2004).

* cited by examiner

*Primary Examiner* — Kara R McMillian

(57) ABSTRACT

The invention discloses compositions of clear injectable solution which comprises Midazolam, pentazocine, tonicity agent, chelating agent, and acids to adjust pH.

14 Claims, No Drawings

STABLE LIQUID INJECTABLE SOLUTION OF MIDAZOLAM AND PENTAZOCINE

TECHNICAL FIELD

The present invention relates to stable liquid injectable solution of Midazolam and Pentazocine. More precisely the invention relates to the composition of clear injectable solution which comprises Midazolam, pentazocine, tonicity agent, chelating agent, and acids to adjust pH. The invention further relates to process for preparation of stable clear liquid injectable solution of Midazolam and pentazocine.

BACKGROUND AND PRIOR ART

Anesthesia is a state of unconsciousness induced in an animal prior to conducting a surgery. The three components of anesthesia include analgesia (pain relief), amnesia (loss of memory) and immobilization. The drugs used to induce anesthesia usually have varying effects in each of these three components. Some drugs may be used individually to achieve all the three components, whereas others have only analgesic or sedative properties and may be used individually for these purposes or in combination with other drugs to achieve full anaesthesia.

Midazolam is a white to light yellow crystalline compound, insoluble in water. The hydrochloride salt of midazolam, which is formed in situ, is soluble in aqueous solutions. Midazolam is a short-acting benzodiazepine central nervous system (CNS) depressant. The effects of Midazolam on the CNS are dependent on the dose administered, the route of administration, and the presence or absence of other medications. Onset time of sedative effects after IM administration in adults is 15 minutes, with peak sedation occurring within 30 to 60 minutes following injection.

Pentazocine is a synthetically-prepared prototypical mixed agonist-antagonist narcotic (opioid analgesic) drug of the benzomorphan class of opioids used to treat moderate to moderately severe pain.

Pentazocine injection is used to relieve moderate to severe pain. It may also be used before surgery or with a general anaesthetic (medicine that puts you to sleep). Pentazocine belongs to the group of medicines called narcotic analgesics (pain medicines). It acts on the central nervous system (CNS) to relieve pain.

Currently available marketed formulation of midazolam is a sterile intravenous solution which is used as intravenous sedative cover before and during minor medical, dental and surgical procedures and for sedation by continuous infusion in patients in intensive care. Since midazolam induces only sedation, management of analgesia by administration of an analgesic agent is required to control the pain during and post-operative surgery.

In relation to above subject there are few prior arts which have tried the combination with midazolam.

US 2011/0046116 A1 describes the combination of midazolam with nicotine useful in eye surgery specifically useful in eye surgery of smokers and heavy smokers. The mixture is injected into the patient prior to eye surgery; nicotine reduces twitching and fidgeting of patients who are smokers and particularly patients who are heavy smokers.

EP 2 450 039 A1 relates to a dosing regimen for sedation with the fast-acting benzodiazepine or a pharmaceutically acceptable salt or solvate thereof for induction of sedation, whereas benzodiazepine is administered in combination with an Opoid. Preferably both drugs are given intravenously and also both drugs are preferably administered in a fixed dose.

Bahadur K. C. and Pokhrel D. described the use of combination of Midazolam; Propofol and Pentazocine for colonoscopy in outdoor patients. Colonoscopies require sedation and analgesia to relieve both anxiety and pain. Propofol and Midazolam combination is used worldwide and allows rapid and profound sedation with quick recovery. Combination of Propofol and Midazolam gives sedation alone without relieving pain, so Pentazocine was used as an analgesic agent along with Propofol and Midazolam.

It is also reported that use of Pentazocine along with Midazolam showed significant reduction in mean dosage of Midazolam required to produce satisfactory sedation when compared to Midazolam alone. Although co-administration of midazolam with Pentazocine was suggested in addition to propofol, however, reports relating to compatibility data for the midazolam with Pentazocine combined in a syringe are not available. The available evidence does not support the use of a fixed-dose of midazolam with Pentazocine combination for procedural sedation and analgesia.

From above references it is evident that there is need for a combination of sedative and analgesic medication to effectively manage not only sedation but also analgesia in operative procedures.

Therefore the object of invention is to provide a stable clear sterile injectable solution of Midazolam and Pentazocine as sedative and analgesic combination.

DETAILED DESCRIPTION OF THE INVENTION

In accordance with the objective, the invention provides the stable sterile injectable solution of Midazolam and Pentazocine.

The rational of the current invention is to provide combination of sedative and narcotic analgesic in a single injection, which can be used as an effective combination therapy in medical, dental, surgical procedures etc.

It is reported that induction of sedation by midazolam injection is more reliable when heavy opiate premedication has been administered or when midazolam is given with narcotic analgesic.

Midazolam injection is also used in combination therapy by intravenous bolus sedation or sedation by continuous infusion in intensive care units.

Accordingly, the invention provides a composition of clear injectable solution which comprises Midazolam 0.5 mg; pentazocine 7.5 mg; tonicity agent, chelating agent, and acids to adjust pH.

The clear injectable solution according to the invention is stable during its shelf life.

In an embodiment, the tonicity agent is selected from sodium chloride or sodium citrate and the chelating agent is Disodium EDTA.

The acids are selected from Lactic acid and Hydrochloric acid. The injectable solution contains 5% v/v Lactic acid and 0.25% v/v Hydrochloric acid. The injectable solution contains 8 mg/ml sodium chloride, 0.1 mg/ml disodium EDTA.

The composition according to the invention comprises lactic acid and hydrochloric acid for pH adjustment. During the preparative process, when dissolved in corresponding acids Midazolam convert to Midazolam hydrochloride in situ and Pentazocine convert to Pentazocine lactate in situ. The pH of the composition is adjusted between 3.0 and 5.0.

In another embodiment, the invention also provides a process for preparation of sterile liquid injectable solution of the combination of Midazolam and Pentazocine which comprises;
1. Dissolving Pentazocine in lactic acid under continuous stirring;
2. Dissolving Midazolam in hydrochloric acid under continuous stirring;
3. Dissolving in another vessel Disodium EDTA and Sodium chloride under stirring;
4. Adding the solutions of step 1 and 2 in solution of step 3 under stirring and adjusting pH of the solution between 3 and 5 and
5. Making the required volume using WFI.

The process of manufacturing the sterile liquid injectable solution can conveniently be carried at ambient temperature. The injectable compositions prepared in accordance with the invention are subjected to accelerated degradation stability studies at variable temperatures viz., 25° C., 30° C. 40° C. and have found that, the assay of the drugs is in the range of 90% to 110% with pH in the range of 3.0 to 5.0 at temperatures 25° C., 30° C. 40° C.

Several different trials of the injectable solutions prepared in accordance with the invention were conducted and tested for the stability. Some of these trials are discussed below in brief.

The following examples, will serve to illustrate the practice of this invention, it being understood that the particulars shown are by the way of examples and for purpose of illustrative discussion of the invention.

Example 1

| Ingredients | Quantity/ml |
| --- | --- |
| Pentazocine | 7.5 mg |
| Midazolam | 0.5 mg |
| Sodium chloride | 8 mg |
| Lactic acid (5% v/v) | Q.S. |
| Hydrochloric acid (0.25% v/v) | Q.S. |
| Water | Q.S. to 1 ml |

Procedure:
1. Dissolving Pentazocine in lactic acid under continuous stirring;
2. Dissolving Midazolam in hydrochloric acid under continuous stirring;
3. Dissolving in another vessel Sodium chloride under stirring;
4. Adding the solutions of step 1 and 2 in solution of step 3 under stirring and adjusting pH of the resulting solution between 3.0 and 5.0 and
5. Making the required volume using WFI;

The results of Stability Study are described in below table:

| | | 3 M | | |
| --- | --- | --- | --- | --- |
| | Initial | 25° C. | 30° C. | 40° C. |
| pH | 4.180 | 4.120 | 4.110 | 4.04 |
| Assay | | | | |
| Pentazocine | 104.8% | 104.74% | 103.9% | 103.7% |
| Midazolam | 105.8% | 105.2% | 105.0% | 104.2% |

Example 2

| Ingredients | Quantity/ml |
| --- | --- |
| Pentazocine | 7.5 mg |
| Midazolam | 0.5 mg |
| Sodium chloride | 8 mg |
| Disodium EDTA | 0.1 mg |
| Lactic acid (5% v/v) | Q.S. |
| Hydrochloric acid (0.25% v/v) | Q.S. |
| Water | Q.S. to 1 ml |

Procedure:

1. Dissolving Pentazocine in lactic acid under continuous stirring;

2. Dissolving Midazolam in hydrochloric acid under continuous stirring;

3. Dissolving in another vessel Sodium chloride and disodium EDTA under stirring 4. Adding the solutions in step 1 and step 2 to the solution of step 3 under stirring and adjusting pH of the resulting solution between 3.0 and 5.0.

5. Making the required volume using WFI.

The results of Stability Study are described in below table:

| | | 3 M | | |
| --- | --- | --- | --- | --- |
| | Initial | 25° C. | 30° C. | 40° C. |
| pH | 4.240 | 4.102 | 4.108 | 4.112 |
| Assay | | | | |
| Pentazocine | 105.47% | 104.32% | 104.14% | 103.89% |
| Midazolam | 106.62% | 106.24% | 106.09% | 105.57% |

Example 3

| Ingredients | Quantity/ml |
| --- | --- |
| Pentazocine | 7.5 mg |
| Midazolam | 0.5 mg |
| Sodium chloride | 8 mg |
| Sodium citrate | 8 mg |
| Lactic acid (5% v/v) | Q.S. |
| Hydrochloric acid (0.25% v/v) | Q.S. |
| Water | Q.S. to 1 ml |

Procedure:

1. Dissolving Pentazocine in lactic acid under continuous stirring;

2. Dissolving Midazolam in hydrochloric acid under continuous stirring;

3. Dissolving in another vessel Sodium chloride and sodium citrate under stirring;

4. Adding the solutions of step 1 and 2 in solution of step 3 under stirring and adjusting pH of the resulting solution between 3.0 and 5.0, and 5. Making the required volume using WFI.

The results of Stability study are described in below table:

|  | Initial | 3 M | | |
|---|---|---|---|---|
|  |  | 25° C. | 30° C. | 40° C. |
| pH | 4.150 | 4.120 | 4.08 | 4.10 |
| Assay |  |  |  |  |
| Pentazocine | 104.8% | 104.2% | 104.1% | 103.6% |
| Midazolam | 104.0% | 103.75% | 103.52% | 102.9% |

We claim:

1. An injectable solution of Pentazocine and Midazolam, comprising:
    an effective amount of Pentazocine;
    an effective amount of Midazolam;
    a pH adjuster, said pH adjuster comprising:
        an amount of lactic acid effective to convert Pentazocine to Pentazocine lactate; and
        an amount of hydrochloric acid effective to convert Midazolam to Midazolam hydrochloride;
    an optional chelating agent; and
    a tonicity agent;
    wherein an assay of Pentazocine and an assay of Midazolam are each between 90% and 110% of an initial value after storage for three months at a temperature of 25° C. to 40° C. and a pH of 3.0 to 5.0.

2. The injectable solution of claim 1, wherein said effective amount of Pentazocine is 7.5 mg/mL.

3. The injectable solution of claim 1, wherein said effective amount of Midazolam is 0.5 mg/mL.

4. The injectable solution of claim 1, wherein the chelating agent is disodium EDTA.

5. The injectable solution of claim 1, wherein the tonicity agent is sodium chloride, sodium citrate, or a mixture thereof.

6. The injectable solution of claim 1, wherein the pH of the injectable solution is between 3.0 and 5.0.

7. A process for preparation of an injectable solution of Pentazocine and Midazolam according to claim 1, which comprises:
    a. Dissolving Pentazocine in a lactic acid solution under continuous stirring;
    b. Dissolving Midazolam in a hydrochloric acid solution under continuous stirring;
    c. Preparing a solution of Sodium chloride and disodium EDTA with stirring;
    d. Adding the Pentazocine solution and the Midazolam solution to the solution of Sodium chloride and disodium EDTA with stirring to form a drug solution;
    e. Adjusting a pH of the drug solution to between 3.0 and 5.0; and
    e. Adjusting the volume of the drug solution with water for injection.

8. The process according to claim 7, wherein the solution contains 8 mg/ml sodium chloride.

9. The process according to claim 7, wherein the solution contains 0.1 mg/ml disodium EDTA.

10. The process according to claim 7, wherein the solution contains 5% v/v Lactic acid.

11. The process according to claim 7, wherein the solution contains 0.25% v/v Hydrochloric acid.

12. The process according to claim 7, wherein the solution contains 8 mg/ml sodium chloride and 0.1 mg/ml disodium EDTA.

13. The process according to claim 7, wherein the solution contains 5% v/v Lactic acid and 0.25% v/v Hydrochloric acid.

14. The injectable solution of claim 1, made by a process comprising:
    a. producing a pentazocine lactate solution by dissolving pentazocine in a lactic acid solution with continuous stirring,
    b. producing a midazolam hydrochloride solution by dissolving midazolam in a hydrochloric acid solution with continuous stirring;
    c. preparing a solution of sodium chloride and disodium EDTA with stirring;
    d. adding the pentazocine lactate solution and the midazolam hydrochloride solution to the solution of Sodium chloride and disodium EDTA with stirring to form a drug solution;
    e. adjusting a pH of the drug solution to between 3.0 and 5.0; and
    e. adjusting the volume of the drug solution with water to produce the injectable solution of Pentazocine and Midazolam.

* * * * *